United States Patent
Lowery et al.

(10) Patent No.: US 12,102,457 B2
(45) Date of Patent: Oct. 1, 2024

(54) MODULAR CASEVAC KIT

(71) Applicant: Government of the United States, as represented by the Secretary of the Air Force, Wright-Patterson AFB, OH (US)

(72) Inventors: Allison Lowery, Huber Heights, OH (US); Peter Voland, Beavercreek, OH (US); Nathan Stover, Xenia, OH (US); Gregory M Burnett, Dayton, OH (US)

(73) Assignee: Government of the United States of America as Represented by the Secretary of the Air Force, Wright-Patterson AFB, OH (US)

( * ) Notice: Subject to any disclaimer, the term of this patent is extended or adjusted under 35 U.S.C. 154(b) by 107 days.

(21) Appl. No.: 17/954,022

(22) Filed: Sep. 27, 2022

(65) Prior Publication Data
US 2024/0099801 A1 Mar. 28, 2024

(51) Int. Cl.
*A61B 50/31* (2016.01)
*B65D 25/10* (2006.01)
*B65D 43/16* (2006.01)

(52) U.S. Cl.
CPC ............ *A61B 50/31* (2016.02); *B65D 25/108* (2013.01); *B65D 43/166* (2013.01); *A61B 2050/311* (2016.02)

(58) Field of Classification Search
CPC .............. A61B 50/31; A61B 2050/311; A61B 57/7445; B65D 25/108; B65D 43/166; A45C 2011/003; A45C 2200/15; A45C 213/025; A45C 13/02; F16M 11/041; F16M 2200/02; A47B 81/061

USPC ....... 206/759, 754, 751, 756, 363, 438, 736, 206/803; 312/223.2, 223.3, 272–276; 190/1, 11, 15.1, 18 R; 248/309.1, 284.1, 248/421, 122.1, 130, 135, 139, 200, 27.1, 248/274.1; 211/175, 150, 80, 81; 220/629, 212, 720; 361/679.01–679.2
See application file for complete search history.

(56) References Cited

U.S. PATENT DOCUMENTS

| | | | | |
|---|---|---|---|---|
| 3,094,948 A | * | 6/1963 | Clow | A47B 27/02 108/119 |
| 3,612,635 A | * | 10/1971 | Uyeda | A01K 97/06 206/315.11 |
| 3,861,328 A | * | 1/1975 | Lawless | A47B 19/06 108/115 |
| 4,032,103 A | * | 6/1977 | Ehrichs | A47B 9/16 248/421 |
| 4,194,628 A | * | 3/1980 | Campos | A61B 50/312 206/570 |
| 4,196,674 A | * | 4/1980 | Van Laarhoven | A47B 27/02 108/4 |

(Continued)

*Primary Examiner* — Chun Hoi Cheung
*Assistant Examiner* — Brijesh V. Patel
(74) *Attorney, Agent, or Firm* — AFMCLO/JAZ; Matthew Fair

(57) ABSTRACT

A protective assembly for medical devices that includes a case having a case base and a case lid, at least one case hinge joins the case base to the case lid, a mounting system contained within the case base. The mounting system further including an enclosure attachment system movably attached to a hardware attachment system by a front rotating pin connector and at least one lockable hardware attachment support.

6 Claims, 5 Drawing Sheets

(56) References Cited

U.S. PATENT DOCUMENTS

| | | | | |
|---|---|---|---|---|
| 4,548,392 A * | 10/1985 | Rickling | | F41A 23/00 |
| | | | | 269/275 |
| 5,400,720 A * | 3/1995 | Stevens | | A47B 9/16 |
| | | | | 248/420 |
| 6,386,393 B1 * | 5/2002 | Paulovich | | B67D 3/0083 |
| | | | | 211/80 |
| 6,427,960 B1 * | 8/2002 | Gehring | | B60N 3/102 |
| | | | | 297/188.14 |
| 6,941,876 B1 * | 9/2005 | Traino | | A47B 23/04 |
| | | | | 108/50.11 |
| 7,063,219 B2 * | 6/2006 | Fann | | A47B 96/025 |
| | | | | 211/74 |
| 7,609,512 B2 | 10/2009 | Richardson et al. | | |
| 7,669,808 B2 * | 3/2010 | Lai | | F16M 11/10 |
| | | | | 248/122.1 |
| 8,356,712 B2 * | 1/2013 | Piazza, Jr. | | A45C 9/00 |
| | | | | 108/14 |
| 8,371,442 B1 * | 2/2013 | Pack | | A45F 3/08 |
| | | | | 206/320 |
| 8,424,825 B2 * | 4/2013 | Somuah | | B60R 11/0252 |
| | | | | 248/316.4 |
| 8,540,109 B1 * | 9/2013 | McPeek | | A45C 13/02 |
| | | | | 206/754 |
| 8,596,728 B2 * | 12/2013 | Rozestraten | | A47B 81/061 |
| | | | | 312/7.2 |
| 8,917,496 B2 | 12/2014 | Richardson et al. | | |
| 8,960,430 B2 * | 2/2015 | Roach | | A45C 13/1084 |
| | | | | 206/370 |
| 8,985,333 B1 * | 3/2015 | Clementi | | F16M 13/00 |
| | | | | 206/476 |
| 9,326,406 B2 * | 4/2016 | Brandt | | H05K 7/00 |
| 9,700,112 B1 | 7/2017 | Samson | | |
| 10,231,795 B1 * | 3/2019 | Johnson | | A47B 97/00 |
| 10,827,827 B1 * | 11/2020 | Failing | | A47B 21/03 |
| 11,320,087 B2 * | 5/2022 | Wojciechowski | | F16M 11/10 |
| 2003/0038047 A1 * | 2/2003 | Sleva | | A61B 50/31 |
| | | | | 206/370 |
| 2004/0020814 A1 * | 2/2004 | Mousset | | A61B 50/31 |
| | | | | 206/438 |
| 2005/0137942 A1 * | 6/2005 | LaFleur | | G07G 1/0018 |
| | | | | 705/26.1 |
| 2006/0278788 A1 * | 12/2006 | Fan | | F16M 11/041 |
| | | | | 248/231.21 |
| 2011/0154889 A1 * | 6/2011 | Stafford | | B29C 45/16 |
| | | | | 264/250 |
| 2012/0025035 A1 * | 2/2012 | Huang | | F16M 11/041 |
| | | | | 248/316.4 |
| 2012/0111875 A1 * | 5/2012 | Johnson | | A47G 23/0216 |
| | | | | 248/346.06 |
| 2012/0220885 A1 * | 8/2012 | Fumuro | | A61B 50/31 |
| | | | | 206/363 |
| 2013/0220859 A1 * | 8/2013 | Roach | | B65D 85/00 |
| | | | | 206/438 |
| 2016/0346056 A1 * | 12/2016 | Demers | | A61B 50/31 |
| 2017/0001784 A1 * | 1/2017 | Jones | | A45C 15/06 |
| 2018/0303456 A1 * | 10/2018 | Tawil | | F16M 11/046 |
| 2020/0323605 A1 * | 10/2020 | Tawil | | A61B 50/33 |
| 2022/0044802 A1 * | 2/2022 | Patel | | G16H 40/63 |
| 2022/0192337 A1 * | 6/2022 | Young | | A45C 13/262 |

\* cited by examiner

MODULAR CASEVAC KIT

RIGHTS OF THE GOVERNMENT

The invention described herein may be manufactured and used by or for the Government of the United States for all governmental purposes without the payment of any royalty.

FIELD OF THE INVENTION

The present invention relates generally to a protective case for protecting medical devices in the field and, more particularly, to suspending the medical devices and supplies within the case with a mounting system.

BACKGROUND OF THE INVENTION

Portable medical devices (PMDs), such as PDAs, computers, wireless hubs, oxygen canisters, monitors, GPS receivers, telematics devices, cell phones, satellite phones, Ventilators, aspirators, fluid pumps, blood warmers and the like are desired to be deployed to fighting forces in harsh environments where they are regularly exposed to harsh environments.

The environments impose harsh conditions that typical PMDs are not designed to accommodate. For example, damage can be done to the PMD through rough handling and dropping. Further, industrial chemicals, grease, water, dirt, and grime may damage or destroy a functioning PMD and inhibit the use of the PMDs valuable data.

It is common to hold the PMDs inside a protective case for transport. However, PMDs are usually removed for use since most cases used for transport are not capable of use while retained in the protective case. A capability to use devices while contained in the protective case for better protection, rapid setup, and rapid closure for transport and/or protection is desired.

SUMMARY OF THE INVENTION

The present invention overcomes the foregoing problems and other shortcomings, drawbacks, and challenges of delivering medical care. While the invention will be described in connection with certain embodiments, it will be understood that the invention is not limited to these embodiments. To the contrary, this invention includes all alternatives, modifications, and equivalents as may be included within the spirit and scope of the present invention.

A protective assembly for medical devices that includes a case having a case base and a case lid, at least one case hinge joins the case base to the case lid, a mounting system contained within the case base. The mounting system further including an enclosure attachment system movably attached to a hardware attachment system by a front rotating pin connector and at least one lockable hardware attachment support.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

The appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

Figure 1:
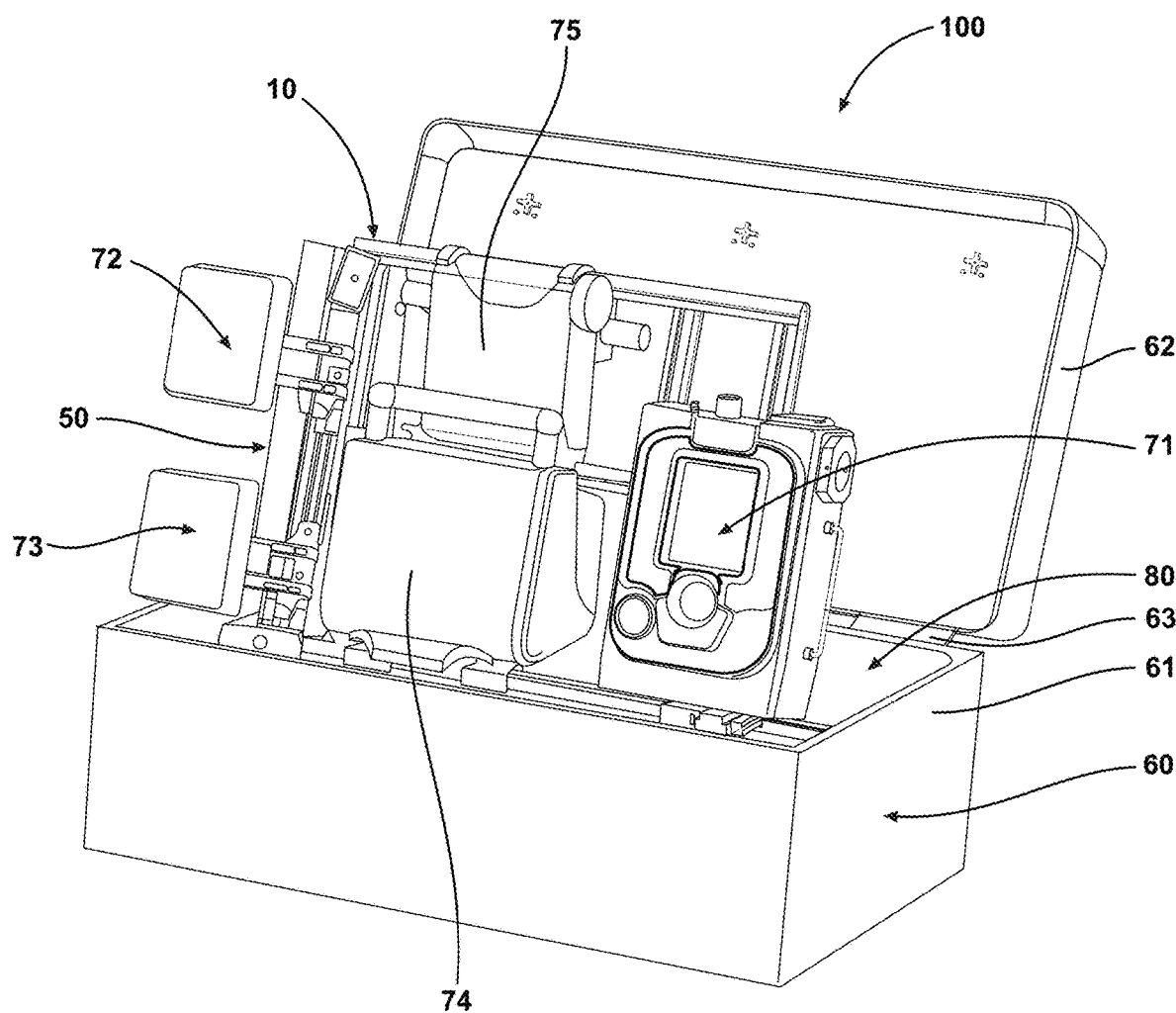
FIG. 1 is a perspective view of an embodiment of the invention shown in the open position.

FIG. 1 is a perspective view of an embodiment of the invention including a protective assembly 100 that may include a rigidly molded case 60 having a case base 61 and a case lid 62. The case base 61 or the case lid 62 may include a carry handle or carry strap (not shown). At least one case hinge 63 joins the case base 61 to the case lid 62. The case is preferably single-man portable, and an all-in-one/grab-n-go kit. The case 60 may be mounted to vehicles, patient tables, walls and the like. The case 60 may be water proof or water resistant and include any closing and securing clasp/latch between the case lid 62 and the case base 61 known in the art (not shown). The case 60 is illustrated open about the case hinge 63. The mounting system 10 is illustrated within and installed in the case base 61.

The case 60, and more specifically the case base 61 may contain a mounting system 10 (detailed in FIG. 5), a power bus 50 (detailed in FIG. 3), available storage 80, a first medical device 71, a second medical device 72, a third medical device 73, a fourth medical device 74 and a fifth medical device 75. The first, second, third and fourth medical device may be any device known in the art including those for measuring medical conditions and those for treating medical conditions. These may include respirators, thermometers, oxygen sensors, blood pressure measurement, heart rate, blood analysis and the like are all potential medical devices contained within the case 60.

Figure 2:
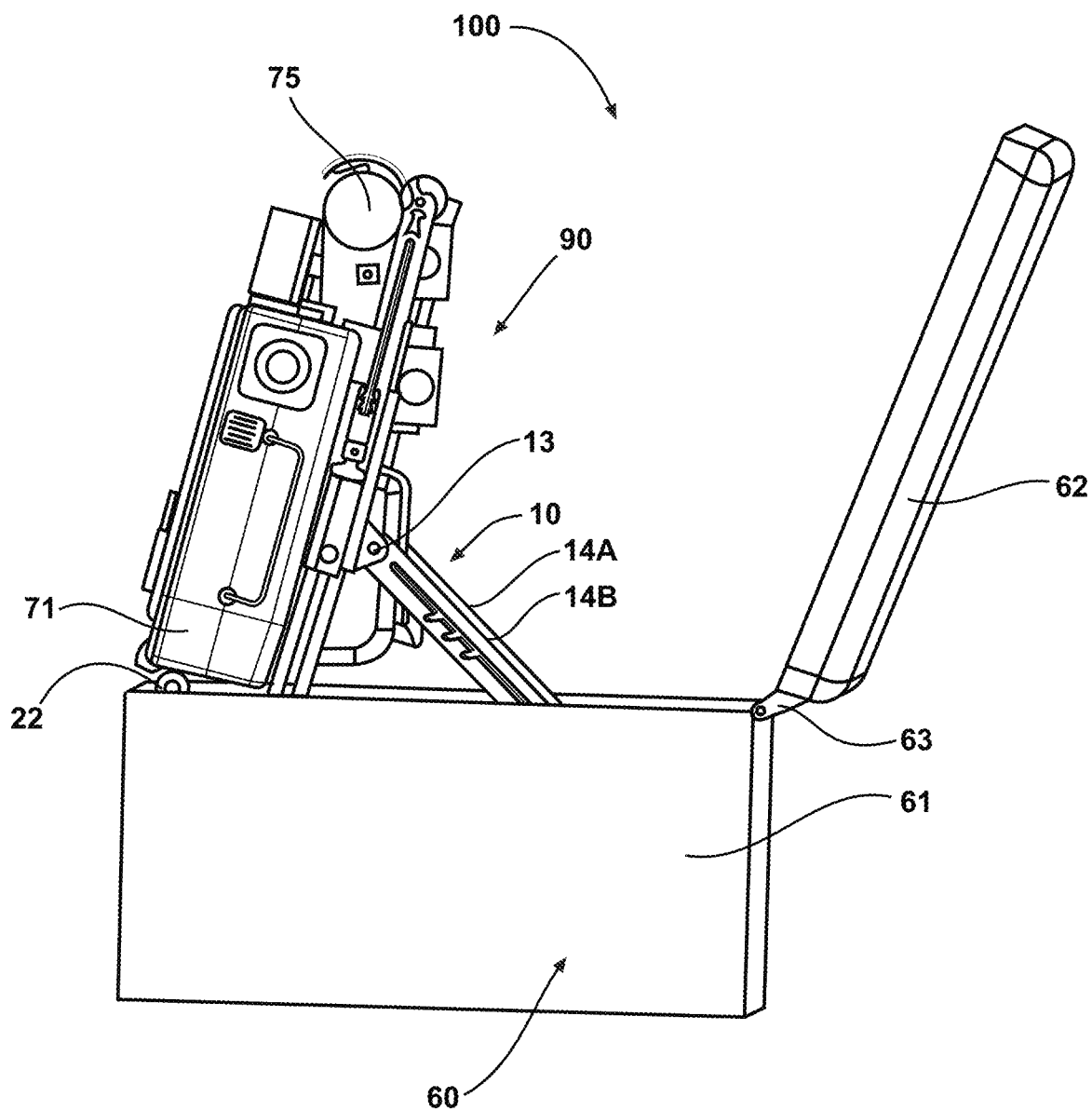
FIG. 2 is a perspective view of an embodiment of the invention shown in the open position.

FIG. 2 is an alternative view of the protective assembly 100 illustrating the case hinge 63 joins the case base 61 to the case lid 62 components of the case 60. FIG. 2 further illustrates an alternate view of the first medical device 71, the fifth medical device 75, all connected to the mounting system 10 which includes the mount pivot pin 13 a front rotating pin connector 22, a first lockable hardware attachment support 14A, a second lockable hardware attachment support 14B and a cable management 90

Figure 3:
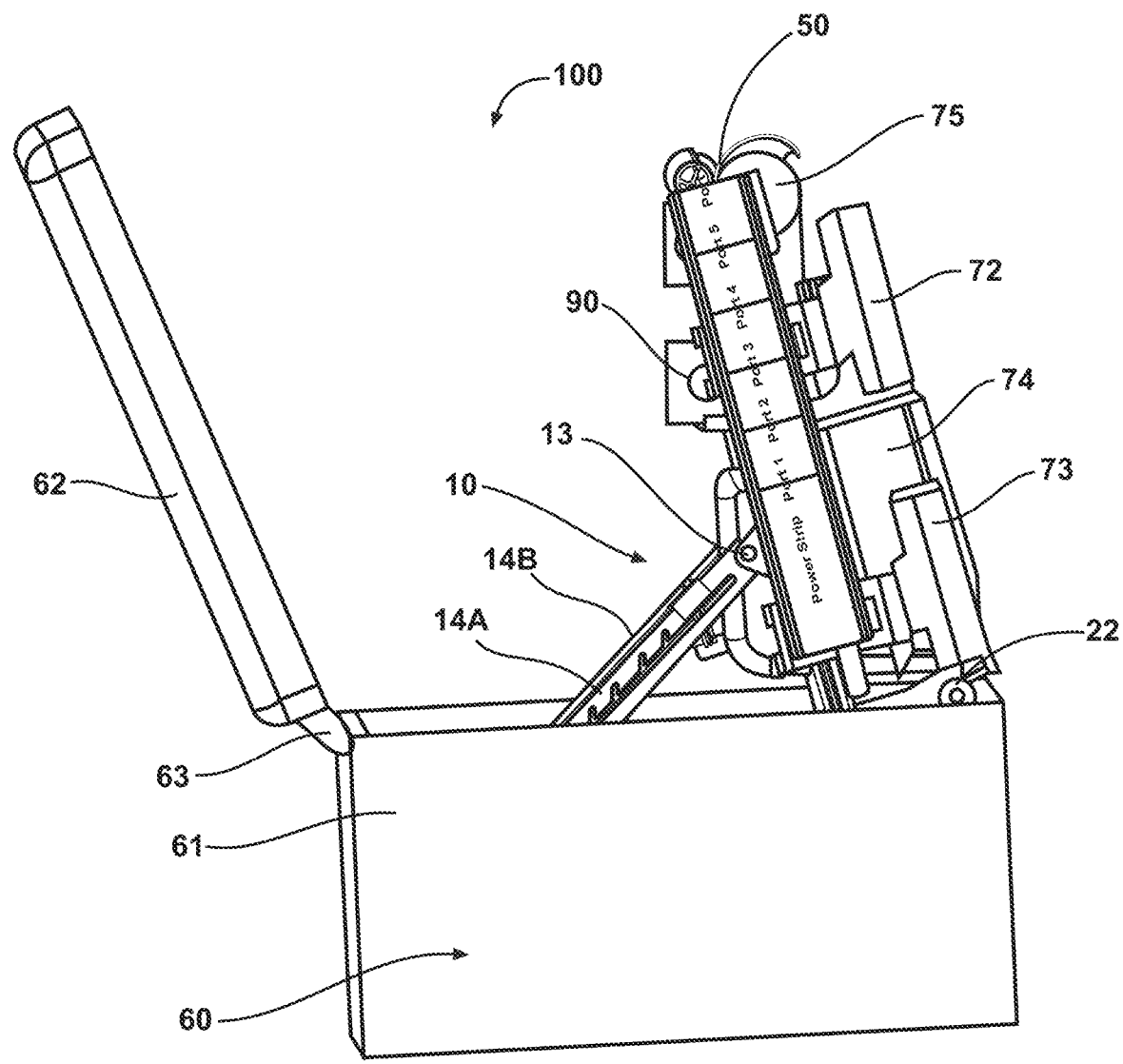
FIG. 3 is a perspective view of an embodiment of the invention shown in an open position.

FIG. 3 is an alternative view of the protective assembly 100 illustrating the case hinge 63 joins the case base 61 to the case lid 62 components of the case 60. FIG. 3 further illustrates an alternate view of the second medical device 72, the third medical device 73, the fifth medical device 75, all connected to the mounting system 10 having the mount pivot pin 13, a front rotating pin connector 22, a first lockable hardware attachment support 14A, a second lockable hardware attachment support 14B and a cable management 90.

Figure 4:
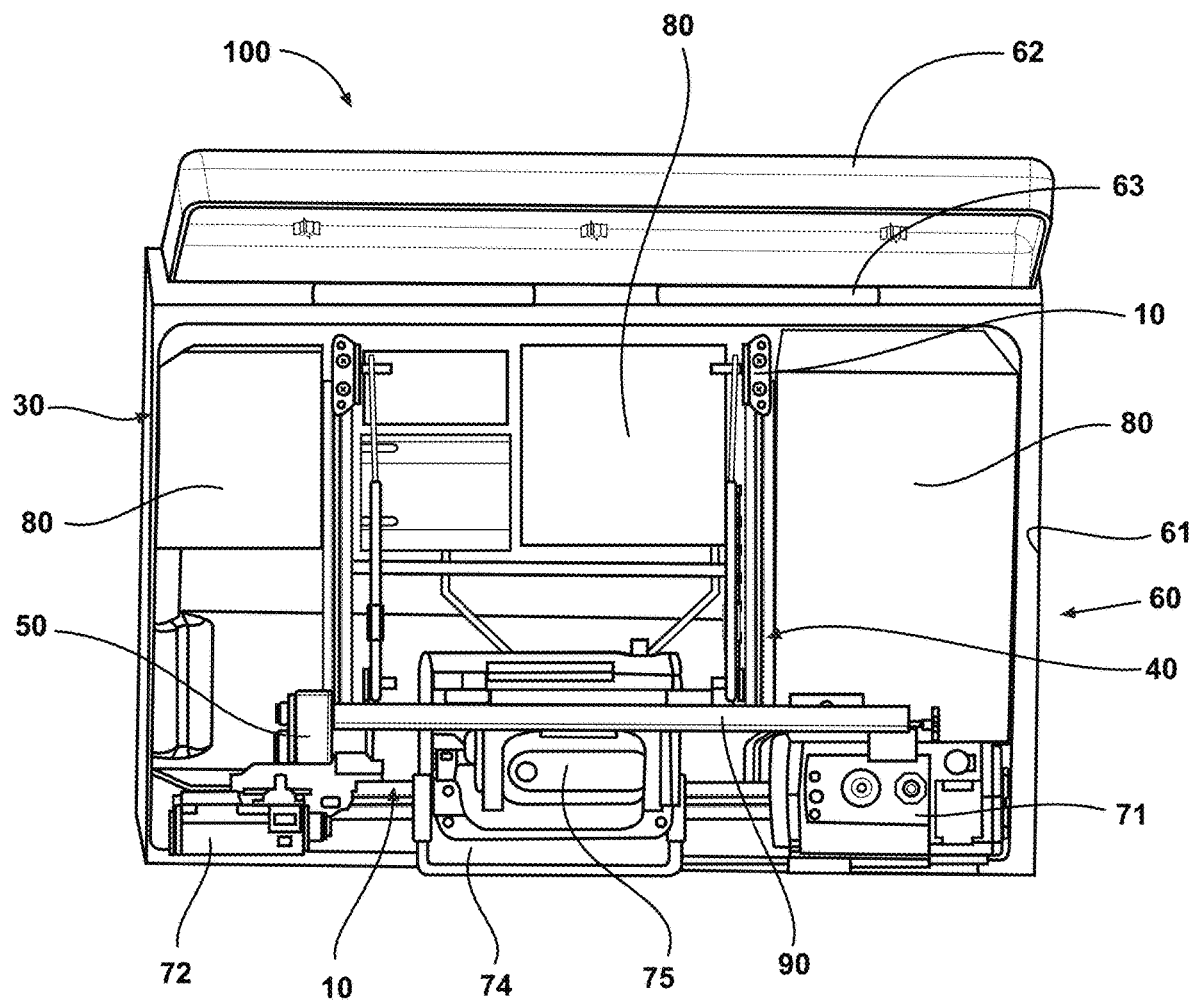
FIG. 4 is a perspective view of an embodiment of the invention shown from above with the container lid open.

FIG. 4 illustrates a perspective view of the protective assembly 100 shown from above with the mounting system 10, hardware attach system 40, and enclosure attachment system 30 in an open but stowed position, awaiting closure by the case lid 62 for travel, or or prior to deployment of the medical devices. FIG. 4 illustrates the case hinge 63 joins the case base 61 to the case lid 62 components of the case 60. FIG. 4 further illustrates an alternate view of the first medical device 71, the second medical device 72, the third medical device 73, the fourth medical device 74 and the fifth medical device 75, all connected to the mounting system 10 and a cable management 90.

Figure 5:
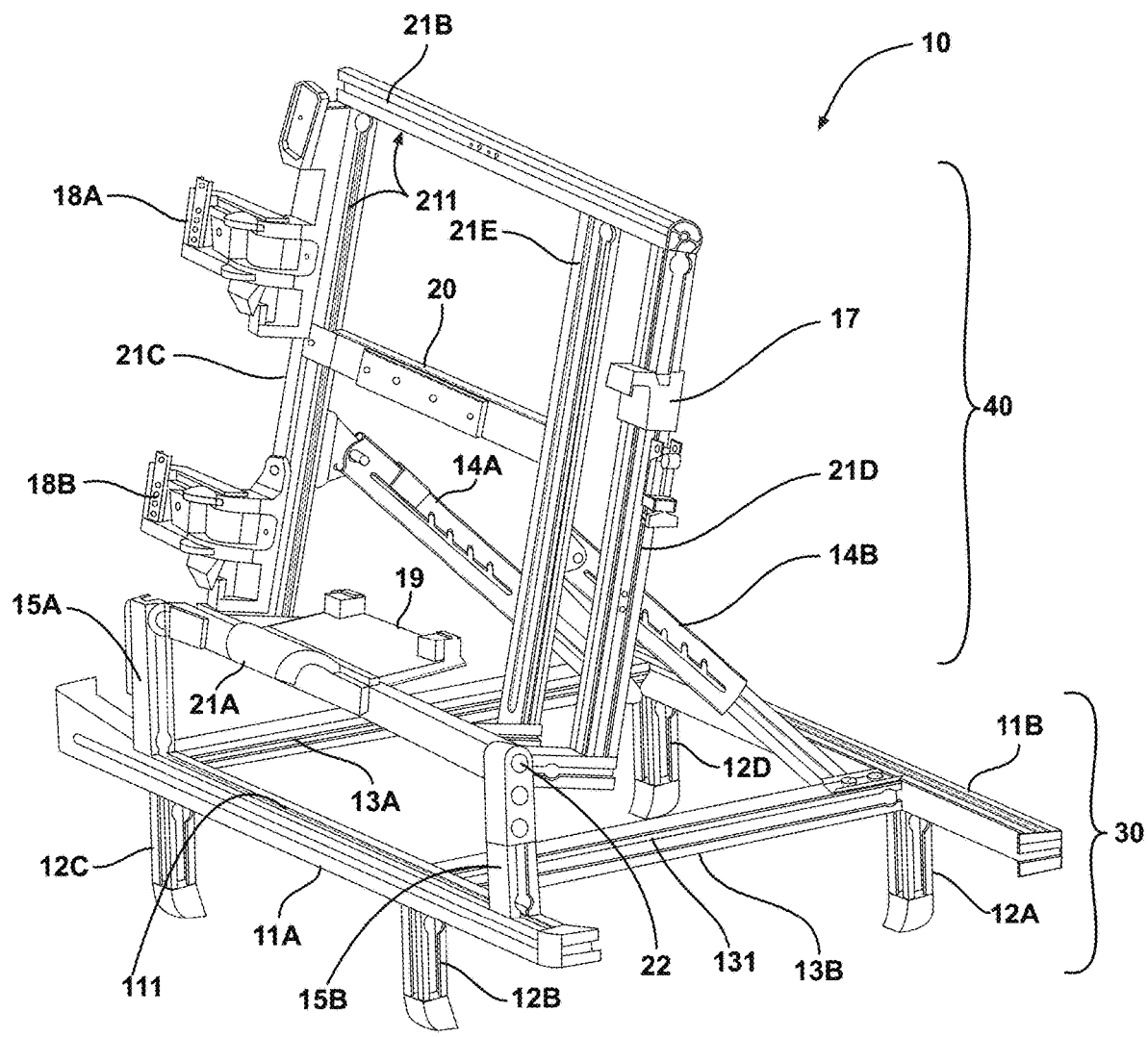
FIG. 5 is an isolated & exploded view of the mount system.

FIG. 5 is an expanded and isolated view of one embodiment of the mounting system 10 that includes an enclosure attachment system 30 movably attached to a hardware attachment system 40. As illustrated in FIG. 5, a plurality of four support legs 12A-12D hold up a front support frame 11A and a rear support frame 11B, where the support frames are connected to a first side support frame 13A and a second side support frame 13B.

As illustrated in FIG. 5 a first riser leg 15A and second riser leg 15B supporting a first equipment mount bar 21A, attaching and supporting the hardware attachment system 40 which may include connected to a second equipment bar 21B by a third equipment mount bar 21C and a fourth equipment mount bar 21D, forming a rectangle as illustrated. A vertically adjustable mount bar 21E may extend between the first equipment mount bar 21A and the second equipment mount bar 21B. An auxiliary support bar 20 may be positioned between the third equipment mount bar 21C and the vertically adjustable mount bar 21E. As illustrated in FIG. 5 an equipment support platform 19 may be moveably attached to the first equipment mount bar 21A. preferably the equipment support platform 19 equipment can be separated from the protective assembly 100 and used on different patients. In one embodiment, a first quick release attachment bracket 18A and/or a second quick release attachment bracket 18B may be used to secure a medical devise to the third equipment mount bar 21C as illustrated in FIG. 5, or any other suitable part of the hardware attachment system 40.

As illustrated in FIG. 5 the front support frame 11A and side support frame 11B elements may include at least one frame slot 111 for movable and mountable hardware attachment of modular medical equipment & supplies. Similarly, as illustrated in FIG. 5 any or all side supports 13A-13B may include at least one side support frame slot 131 for movable and mountable hardware attachment of modular medical equipment & supplies. As illustrated in FIG. 5 any or all mounting equipment mount bars 21A-21D may include at least one mount bar slot 211 for movable and mountable hardware attachment of modular medical equipment & supplies.

A slider 17 is slidingly attached to the mount bar 21D and is used in conjunction with a toggle clamp (not shown) that can restrict sliding movement when in a locked position. The slider 17 is sliding movable and can be locked on the mounting system 10 to help secure the hardware attachment system 40.

The attachment brackets and equipment support platform (s) may be secured by any suitable means known in the art including magnetic attachments, clip in attachments, screws, bolts, pins, clasps and the like. They are preferably held in place when the case is closed, and movable once opened by sliding or rotating about the front rotating pin connector 22 which allows the hardware attachment system 40 to rotate. In one embodiment the mounting system will auto guide to their position such that items pulled out, rest at a predetermined location for consistent access, day or night.

The hardware attachment system 40 may raise and lower within the case base 61 by at least one lockable hardware attachment support. As illustrated in FIG. 5, the mounting system 10 may include a first lockable hardware attachment support 14A and a second lockable hardware attachment support 14B, both extendable, retractable and lockable to hold the plurality of medical devices in the desired deployed or stowed configuration. In one embodiment the first lockable hardware attachment support 14A and the second lockable hardware attachment support 14B may use a hydraulic, rather than mechanical system to be raise to its operating location. In an alternate embodiment the first lockable hardware attachment support 14A and the second lockable hardware attachment support 14B may automatically raise to its operating location when the case lid 62 is raised from the case base 61.

When deployed for use, the plurality of medical devices may be movable to accommodate visibility and the environment as appropriate.

The mounting system 10 may be adjustable to fit a range of case 60 sizes. In one embodiment the mounting system 10 may be dropped into a standard case 60 size. In one embodiment the mounting system may be held in the case by friction to avoid breaching the integrity of the case 60. Alternatively, fasteners between the case 60 and the mounting system 10 may be used.

The medical devices include any medical device known in the art and may include such devices as self-contained IV bag/infusion hangers (LR, medicines) or oxygen support equipment. They may also include communication devices (radios, cell phones, satellite phones, and the like), computers displays or other electronics as needed for the operation. Any of the above may include a touch screen. The medical devices may be independent or interconnected for automatic data analysis or other purpose. The foregoing description of the term medical device has been presented for purposes of illustration and description. It is not intended to be exhaustive or to limit the invention to the precise forms disclosed, and other modifications and variations may be possible in light of the teachings of this specification.

Case 60 provides a protective encasement of the medical equipment and supplies therein. The case 60 may be designed to be watertight, chemically resistant, and otherwise protect the contents when transported, dropped or under compressive loads.

The case 60 may include a clasp between the case base 61 and case lid 62 (not shown). The clasp may be any functional location, and any means known in the art to secure the case base 61 and case lid 62 in a closed position. In one embodiment the clasp mechanism may be the sides of the case opposite the hinge 63.

The case 60 may be constructed of rigid plastic, metal, rubber, or any other type of material known in the art that could be adapted to afford the protection of medical devices enclosed. Further, the appropriate selection of material for the case 60 may be designed to enable various communication transmissions known in the art.

The protective cover of the present invention may have device connections (not illustrated) through the cover for connecting through the case. Such a connection may be for power, communication, system integration with other devices (medical devices) and the like. The connections may be any means known in the art.

While the present invention has been illustrated by a description of one or more embodiments thereof and while these embodiments have been described in considerable detail, they are not intended to restrict or in any way limit the scope of the appended claims to such detail. It is not intended to be exhaustive or to limit the invention to the precise form disclosed, and other modifications and variations may be possible in light of the above teachings. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept. It is intended that the appended claims be construed to include other alternative embodiments of the invention except insofar as limited by the prior art.

What is claimed is:

1. A protective assembly for medical devices that includes a case having a case base and a case lid;
   at least one case hinge joins the case base to the case lid;
   a mounting system contained within the case base, the mounting system further including an enclosure attachment system movably attached to a hardware attachment system by a front rotating pin connector and at least one lockable hardware attachment support;
   wherein the enclosure attachment system further includes a plurality of support legs supporting a front support frame and a rear support frame, and a first side support frame and a second side support frame connected to the front and rear support frame;
   wherein, a first riser leg and a second riser leg support the hardware attachment system; and
   wherein the hardware attachment system further includes a first equipment mount bar connected to a second equipment bar by a third equipment mount bar and a fourth equipment mount bar.

2. The protective assembly for medical devices of claim 1 wherein the hardware attachment system further includes a vertically adjustable mount bar extends between the first equipment mount bar and the second equipment mount bar.

3. The protective assembly for medical devices of claim 2 wherein the hardware attachment system further includes an auxiliary support bar positioned between the third equipment mount bar and the vertically adjustable mount bar.

4. The protective assembly for medical devices of claim 3 wherein the hardware attachment system further includes an equipment support platform moveably attached to the first equipment mount bar.

5. The protective assembly for medical devices of claim 4 wherein the hardware attachment system further includes at least one quick release attachment bracket to secure at least one medical devise to the third equipment mount bar.

6. The protective assembly for medical devices of claim 4 wherein the front support frame includes a first frame slot and the side support frame includes a second frame slot.

* * * * *